US00PP11310P

United States Patent [19]

Kearley, Jr.

[11] Patent Number: Plant 11,310

[45] Date of Patent: Mar. 21, 2000

[54] LANTANA PLANT NAMED 'ANNE MARIE'

[75] Inventor: Richard C. Kearley, Jr., Hawthorne, Fla.

[73] Assignee: Robrick Nursery, Inc., Hawthorne, Fla.

[21] Appl. No.: 09/153,431

[22] Filed: Sep. 14, 1998

[51] Int. Cl.[7] ..... A01H 5/00

[52] U.S. Cl. ..... Plt./227

[58] Field of Search ..... Plt./227

[56] References Cited

U.S. PATENT DOCUMENTS

P.P. 10,156 12/1997 Roberson ..... Plt./227

P.P. 10,856 4/1999 Covington ..... Plt./227

*Primary Examiner*—Howard J. Locker

*Assistant Examiner*—Kent L. Bell

*Attorney, Agent, or Firm*—C. A. Whealy

[57] ABSTRACT

A distinctive cultivar of Lantana plant named 'Anne Marie', characterized by its compact, dense, bushy and outwardly spreading growth habit; pubescent stems and leaves; very dark green leaves; numerous inflorescences; initially bright yellow petals that become various shades of dark pink to purple during development; and good weather tolerance.

2 Drawing Sheets

BACKGROUND OF THE INVENTION

The present invention relates to a new and distinct cultivar of Lantana plant, botanically known as *Lantana camara*, and hereinafter referred to by the cultivar name 'Anne Marie'.

The new Lantana was discovered by the Inventor in Hawthorne, Fla., as a naturally-occurring whole plant mutation of the nonpatented *Lantana camara* cultivar 'Irene', and was observed as a single plant in a group of plants of the parent cultivar during the Spring of 1996.

Asexual reproduction of the new Lantana by softwood cuttings in Hawthorne, Fla., has shown that the unique features of this new Lantana are stable and reproduced true to type in successive propagations.

SUMMARY OF THE INVENTION

The new Lantana has not been observed under all possible environmental conditions. The phenotype may vary significantly with variations in environment such as temperature and light and fertility levels, without, however, any variance in genotype.

The following traits have been repeatedly observed and are determined to be the unique characteristics of plants of the new Lantana and differentiate plants of the new Lantana from other commercial Lantana cultivars known to the Inventor:

1. Plants of the new Lantana are compact, dense and bushy with an outwardly spreading growth habit.

2. Plants of the new Lantana have pubescent stems and leaves.

3. Plants of the new Lantana have very dark green leaves.

4. Plants of the new Lantana are very floriferous.

5. Flowers of plants of the new Lantana are bright yellow after opening, become various shades of dark pink to purple during development and fade to light pink.

6. Plants of the new Lantana exhibit good weather tolerance and are very tolerant to high temperatures.

Plants of the new Lantana can be compared to plants of the parent cultivar, 'Irene'. However in side-by-side comparisons conducted in Howthorne, Fla., and Keller, Tex., plants of the new Lantana differ from plants of the cultivar Irene in the following characteristics:

1. Plants of the new Lantana are more compact than plants of the cultivar 'Irene'.

2. Plants of the new Lantana are outwardly spreading whereas plants of the cultivar 'Irene' are upright and open in plant habit.

3. Plants of the new Lantana are denser and more freely branching than plants of the cultivar 'Irene'. Plants of the new Lantana do not require pinching whereas plants of the cultivar 'Irene' require pinching to produce full plants.

4. Plants of the new Lantana have smaller leaves than plants of the cultivar 'Irene'.

5. Plants of the new Lantana have shorter internodes than plants of the cultivar 'Irene'.

6. Plants of the new Lantana are more floriferous than plants of the cultivar 'Irene'.

Plants of the new Lantana can also be compared to plants of the cultivar, 'Robcomplan', disclosed in U.S. Plant Pat. No. 9,837. However in side-by-side comparisons conducted in Hawthorne, Fla., and Keller, Tex., plants of the new Lantana differ from plants of the cultivar 'Robcomplan' in the following characteristics:

1. Plants of the new Lantana grow faster and are larger and much more vigorous than plants of the cultivar 'Robcomplan'.

2. Plants of the new Lantana are outwardly spreading whereas plants of the cultivar 'Robcomplan' are upright in plant habit.

3. Plants of the new Lantana have larger and broader leaves than plants of the cultivar 'Robcomplan'.

4. Plants of the new Lantana have longer internodes than plants of the cultivar 'Robcomplan'.

5. Plants of the new Lantana have larger inflorescences than plants of the cultivar 'Robcomplan'.

BRIEF DESCRIPTION OF PHOTOGRAPHS

The accompanying colored photographs illustrate the overall appearance of the new Lantana, showing the colors as true as it is reasonably possible to obtain in colored reproductions of this type. The photograph on the first sheet comprises a side perspective view of a typical plant of 'Anne Marie' grown in a one-gallon container. The photograph on the second sheet comprises a side perspective view of typical plants of the cultivars 'Irene', 'Robcomplan', and 'Anne Marie' (left to right) grown in one-gallon containers showing the differences in plant size and growth habit. Actual flower and foliage colors may differ from flower and foliage colors in the photographs due to light reflectance.

DETAILED BOTANICAL DESCRIPTION

The following observations, measurements and values describe plants grown in Hawthorne, Fla., and Keller, Tex., under conditions which approximate commercial practice. Single plants were grown in one-gallon containers under conditions which closely approximate commercial production conditions. In the following description, color references are made to The Royal Horticultural Society Colour Chart except where general terms of ordinary dictionary significance are used.

Botanical classification: *Lantana camara* cultivar 'Anne Marie'.

Parentage: Naturally-occurring whole plant mutation of nonpatented *Lantana camara* cultivar 'Irene'.

Propagation:

*Type.*—By softwood cuttings.

*Time to initiate roots.*—About 14 days at temperatures of 24 to 32° C.

*Time to develop roots.*—About 30 days at temperatures of 24 to 32° C.

*Rooting habit.*—Fine, freely branching, fibrous.

Plant description:

*Plant form and growth habit.*—Perennial shrub with outwardly spreading and horizontal growth habit. With subsequent growth, plant habit may become decumbent. Very freely branching, plants dense and bushy with short internodes; pinching is typically not required to produce full plants. Flowers abundant and flowering continuous.

*Growth rate/crop time.*—Relatively rapid growth rate. After planting rooted cuttings into one-gallon containers, about six weeks are required to produce finished plants. Plants of the new Lantana typically do not require growth retardants.

*Plant height.*—About 17 cm.

*Plant width.*—About 42 cm.

*Stem description.*—Lateral branch diameter: About 5 mm. Internode length: About 2 cm. Strength: Relatively rigid. Stem color: Immature, greener than 144A; Mature, woody, brownish gray. Stem texture: Pubescent; coarse white hairs.

*Foliage description.*—Arrangement: Opposite. Length: About 5.7 cm. Width: About 4.2 cm. Shape: Ovate. Apex: Acute. Base: Obtuse to truncate. Margin: Serrate. Aspect: Flat to concave. Texture: Very rough; coarse white hairs on both surfaces. Color: Young foliage, upper surface: 147A. Young foliage, lower surface: 147B. Mature foliage, upper surface: Close to 147A. Mature foliage, lower surface: Close to 147B. Petiole length: About 1.25 cm. Petiole diameter: About 2 mm. Petiole color: Greener than 144A.

Flower description:

*Flowering habit.*—Scalloped flowers arranged in terminal and axillary inflorescences. Numerous inflorescences per plant; number of inflorescences depends on plant size and number of lateral branches developed. Several inflorescences per lateral branch in flower simultaneously. Flowers held upright and are not persistent.

*Natural flowering season.*—Early spring until late fall; flowering continuous.

*Quantity of flowers.*—Numerous, usually about 21 flowers per head.

*Inflorescence/flower size.*—Inflorescences about 3.7 cm in diameter; individual flowers about 1 cm in diameter and about 1.4 cm in height.

*Peduncle.*—Peduncle angle: About 45° to stem. Strength: Flexible, but hold inflorescences upright. Texture: Pubescent. Color: 144A.

*Flower bud.*—Diameter: About 6 mm. Length: About 6 mm.

*Petals.*—Arrangement: Typically four, occasionally five fused at base. Shape: Rounded, scalloped. Length: About 5 mm. Width: About 4 mm. Tube length: About 1.3 cm. Tube diameter: About 2 mm. Apex: Rounded. Margin: Minutely fringed. Aspect: Flat and perpendicular to tube or slightly upright. Texture: Smooth. Color: Before opening: Purple, 61A, to 53B/53C. Open flowers: Upper surface: Initially bright yellow, 9A; becoming reddish pink, 53B/53C; to purple, 61A; fading to light pink, 62A/62B. Lower surface: Initially light yellow, 10B/10C; then becoming light pink, close to 62C. Tube: Close to 53B/53C.

*Sepals.*—Shape: Lanceolate. Length: About 7.5 mm. Diameter: About 2 mm. Apex: Acute. Margin: Entire. Texture: Pubescent. Color: Close to 147A.

*Reproductive organs.*—Stamens: Quantity: Usually four. Anther shape: Bilobate. Anther length: About 0.75 mm. Pollen color: Yellow, close to 9A. Pistils: Length: About 3.5 mm. Stigma color: Light green. Style color: Light green.

*Fruit.*—Diameter About 5 mm. Texture: Initially smooth, wrinkled when dry. Color: Immature, green, darker than 141A; mature, black.

Disease resistance: Plants of the new Lantana have not exhibited susceptibility to pathogens common to Lantana.

Weather tolerance: Plants of the new Lantana exhibit good weather tolerance with very good tolerance to high and low temperatures typical of zones 7 to 10 (U.S.D.A. Hardiness Zone Map).

It is claimed:

1. A new and distinct Lantana plant named 'Anne Marie', as illustrated and described.

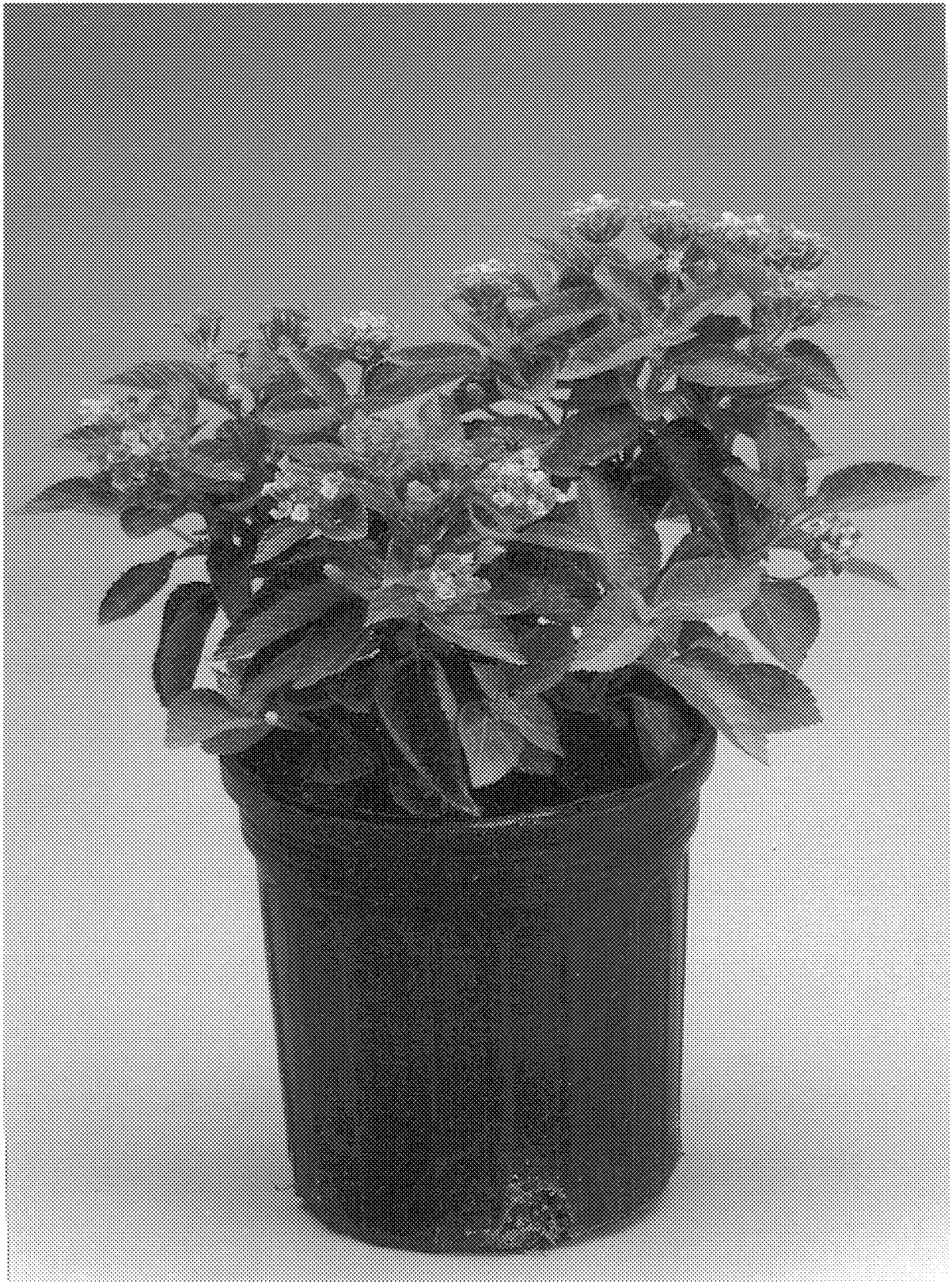

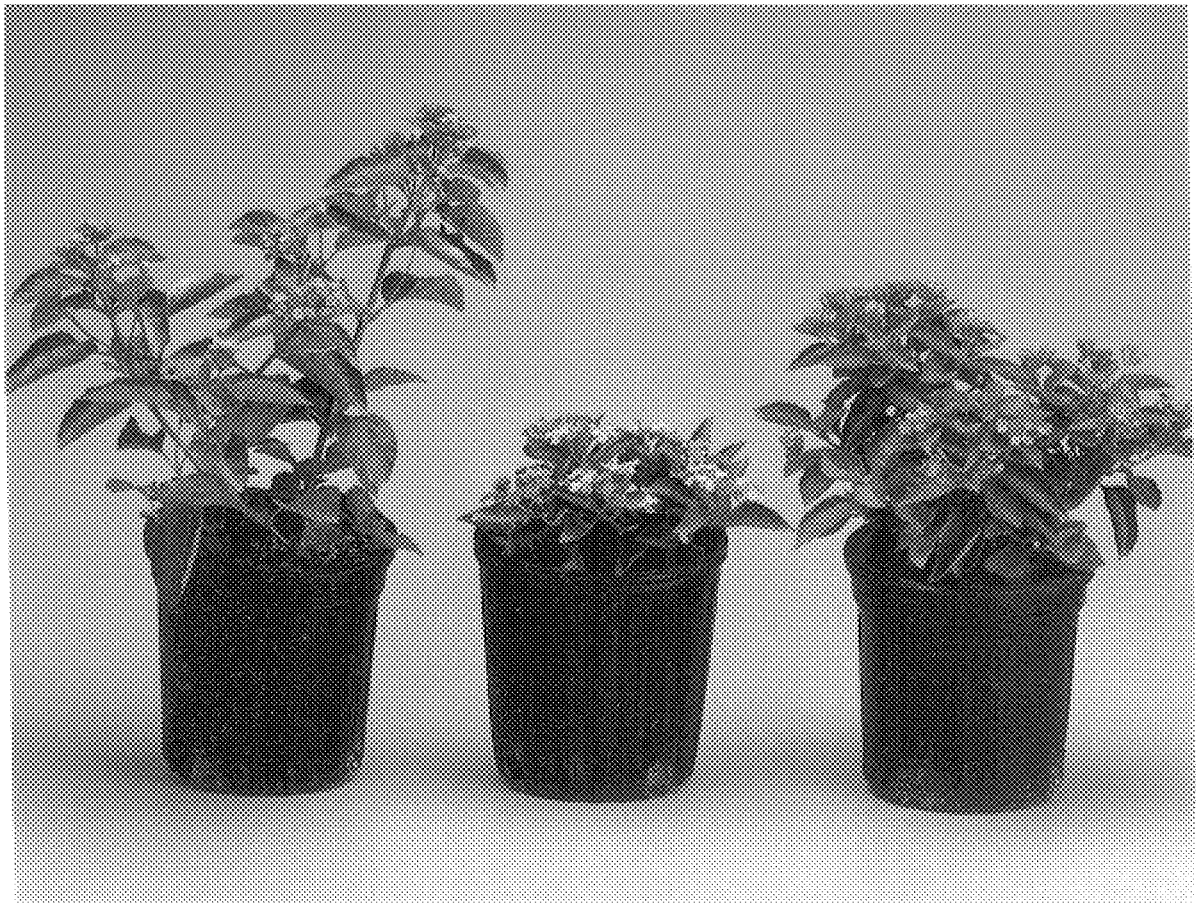

* * * * *